United States Patent
Kyle et al.

(10) Patent No.: US 6,660,754 B1
(45) Date of Patent: Dec. 9, 2003

(54) METHOD FOR REDUCING OR ELIMINATING SMOKING

(75) Inventors: Theodore K. Kyle, Pittsburgh, PA (US); Saul Shiffman, Pittsburgh, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/504,560

(22) Filed: Feb. 15, 2000

(51) Int. Cl.[7] ............................. A61K 31/44; A61K 9/68
(52) U.S. Cl. ..................... 514/343; 514/813; 424/48; 424/440
(58) Field of Search ......................... 514/343, 813; 424/48, 440

(56) References Cited

U.S. PATENT DOCUMENTS 5,055,478 A     10/1991   Cooper et al. .............. 514/343
5,488,962 A     2/1996    Perfetti ...................... 131/270

OTHER PUBLICATIONS

Cinciripini et al., "The Effects of Smoking Schedules on Cessation Outcome: Can We Improve on Common Methodsof Gradual and Abrupt Nicotine Withdrawal?", *Journal of Consulting and Clinical Psychology*, vol. 63, No. 3, pp. 388–399 (1995).
U.S Department of Health and Human Services, AHCPR Publication No. 96–0692, "Smoking Cessation", Apr. 1996.
Physicians' Desk Reference, SmithKline Beecham Consumer. Pp. 3016–3017, 1999 (entire document).

*Primary Examiner*—Theodore J. Criares
*Assistant Examiner*—Jennifer Kim
(74) *Attorney, Agent, or Firm*—Andrea L. Winslow; Theodore R. Furman, Jr.; Charles M. Kinzig

(57) ABSTRACT

This invention is an improved method for reducing or eliminating tobacco usage and the nicotine dependency associated with tobacco usage by gradually decreasing an individual's tobacco consumption over a time period while replacing nicotine from tobacco with an alternative nicotine source.

11 Claims, No Drawings

METHOD FOR REDUCING OR ELIMINATING SMOKING

BACKGROUND OF THE INVENTION

The present invention relates to a method for gradually reducing or eliminating an individual's tobacco usage habit, in particular smoking, as well as the associated nicotine dependence that is created by tobacco use.

The idea of applying reduction strategies to smoking cessation has been explored in the development of smoking cessation methods over the last twenty years. However, reduction as an end goal or as a means to cessation has received very little attention in recent years. In fact, these methods are not even included as treatment options in the Agency for Health Care Policy and Research (AHCPR) Centers for Disease Control and Prevention Smoking Cessation Guideline, the authoritative review that outlines the standard of care for smoking cessation. See U.S. Department of Health and Human Services, AHCPR Publication No. 96-0692, Apr. 1996.

Innovative treatments of smoking reduction or cessation are significantly lacking. Most smoking control methods are cessation methods and are undertaken without the aid of pharmacological or behavioral therapy, in part because the quitting approaches associated with these therapies are not consistent with a smoker's preferred quitting approach. Recent research on smoker's attitude toward quitting shows that in comparison to abrupt cessation, many smokers who are interested in quitting smoking prefer to quit by gradually reducing the amount they smoke. Recent studies demonstrate that gradual reduction strategies can succeed without pharmacological therapy. These strategies, however, involve intensive behavioral intervention and always have as their goal smoking cessation rather than reduction only. For example, see Cinciripini et al., "The Effects of Smoking schedules on Cessation Outcome: Can We improve on Common Methods of Gradual And Abrupt Nicotine Withdrawal," *Journal of Consulting and Clinical Psychology*, Vol. 63, No. 3, pp. 388–399 (1995), comparing two gradual reduction quitting methods to quitting "cold turkey." The gradual reduction methods of quitting described in Cinciripini et al. included (1) progressively increasing inter-cigarette intervals and (2) gradually reducing the number of cigarettes smoked without changing the inter-cigarette interval. All methods included the use of cognitive-behavioral relapse prevention training, and were without pharmacological therapy such as an alternative nicotine source.

These efforts to quit by gradual reduction without nicotine replacement often fail. It has been suggested that one reason that gradual reduction fails is because tobacco users are progressively deprived of nicotine and consequently experience nicotine cravings and withdrawal which deter quitting or further reduction.

One method that combines reduction with the use of nicotine replacement therapy is described in U.S. Pat. No. 5,055,478. In one embodiment, the method described in this patent includes the steps of first recording over an approximately two week period, the times during which each cigarette is consumed. These time periods of smoking are referred to as consumption periods, which are not necessarily consecutive in time. Then, tobacco consumption gradually is decreased by replacing in an increasing number of consumption periods (up to 16 consumption periods) over a two week period, the use of tobacco with an alternative nicotine source such as Nicorette® nicotine-containing chewing gum (2 mg nicotine dosage), until no further tobacco is consumed. The nicotine in each piece of gum is a substitute for all the tobacco consumed during a consumption period. This level of consumption of the alternative nicotine source is maintained for approximately four weeks. During this four week period, while the individual is still receiving nicotine through the alternative nicotine source, the individual addresses the social and psychological reasons for smoking. After the four week period, the alternative nicotine source is eliminated at a rate of one consumption period per week for approximately 14–16 weeks, until no further alternative nicotine source is consumed.

A second method described in U.S. Pat. No. 5,055,478 includes an initial step of recording for approximately two weeks an individual's normal tobacco consumption pattern to identify the times of day during which tobacco is consumed, and the amount of tobacco consumed during these periods. Each day is then broken down into consumption periods of one hour each. Then, all tobacco consumption is abruptly stopped and an alternative nicotine source (approximately 1.5 to 1.75 mg. per consumption period) is administered for a period of about two weeks. As with the first method above, following cessation of smoking but while the individual is still receiving nicotine through the alternative nicotine source, the individual addresses the social and psychological reasons for smoking. The user then gradually decreases administration of the alternative nicotine source down to a lower level of approximately 1 mg per consumption period for approximately 10–18 days. This is done by administering the lower dosage alternative nicotine source during an increasing number of consumption periods until the lower dosage is consumed during all consumption periods. After reaching the lower dosage in each consumption period, the lower dosage alternative nicotine source is administered for about two weeks. Then, the user gradually eliminates consumption of the alternative nicotine source by eliminating consumption of the source during an increasing number of consumption periods (one per week) a until no alternative nicotine source is consumed.

Another method closely related to the methods described in U.S. Pat. No. 5,055,478, combines smoking reduction with the use of nicotine replacement therapy. This method is described in Cooper et al., "New Hope for Heavy Smokers—The Cooper/Clayton Method to Stop Smoking". In this method, after the initial two week recordation phase, an alternative nicotine source is substituted for all consumption periods, and the individual immediately stops smoking. The remainder of the method is similar to the above method but elimination of the alternative nicotine source is to a maintenance level which is about one-third of the first maintenance level, followed by gradual reduction as in the final phase described above. In this method, the individual receives intensive person-to-person psychological intervention.

Yet another method of smoking cessation is described in a publication by SmithKline Beecham entitled "Nicorette® Committed Quitters™ Calendar and Smoking Cessation Service. In this method, the user abruptly stops smoking and consumes one piece of Nicorette® gum (2 mg. or 4 mg. dosage, generic name nicotine polacrilex gum) every 1–2 hours consuming no more than 24 pieces per day for a six week period. In week seven the individual cuts back to consuming one piece of Nicorette® gum every two hours and continues at this level for three weeks. In week 10, the individual cuts back to one piece of Nicorette® gum every four hours. After week 12, the individual stops using Nicorette® gum. During the twelve week period, the individual records the number of pieces of Nicorette® gum chewed and some activities the individual plans to do each day to help cope with not smoking. The calendar also provides helpful hints for dealing with cravings and the psychological aspects of quitting smoking, and a reminder of the amount of time invested in quitting.

SUMMARY OF THE INVENTION

This invention is an improved method for reducing or eliminating tobacco usage, particularly smoking, and the nicotine dependency associated with tobacco usage by gradually decreasing an individual's tobacco usage over a time period while replacing nicotine from tobacco with an alternative nicotine source.

DETAILED DESCRIPTION OF THE INVENTION

The present invention as described herein, is a method to reduce or eliminate an individual's tobacco usage habit, in particular smoking, as well as the nicotine dependency associated with that habit. The method includes the step of gradually decreasing tobacco usage over a time period until the individual significantly reduces or eliminates tobacco usage. The reduction or elimination of tobacco usage is accomplished with or without behavioral intervention using nicotine replacement therapy such as an alternative nicotine source in conjunction with gradual tobacco use reduction. Such a strategy expands the use of nicotine replacement therapy from an abrupt tabacco usage cessation to a gradual reduction. Gradually reducing the number of cigarettes smoked or other nicotine products used while replacing nicotine from tobacco with an alternative nicotine source aids in reducing nicotine cravings and withdrawal thereby facilitating reduction or elimination of tobacco usage.

The alternative nicotine source can be any substance that contains nicotine and can be administered orally, systemically, through the mucous membranes, or otherwise that will deliver a dosage of nicotine approximating that delivered through smoking cigarettes or using another. Examples include suppository, snuff, inhaler, nasal spray, lozenge, sucker or the like. A preferred alternative nicotine source is a nicotine-containing chewing gum such as a nicotine polacrilex gum, preferably in about 2 mg. to about 4 mg. dosage based on the content of nicotine source.

Preliminary research conducted using the present invention provides clinical evidence that the present invention is effective in permitting smokers to reduce smoking and, when used in a regimen involving smoking reduction, is more effective than placebo in permitting smokers to cease smoking.

In one embodiment of the present invention, nicotine gum (2 mg. or 4 mg. dosage) is administered to a smoker who is instructed as follows:

(a) On day one, chew one piece of nicotine containing gum after waking, then wait one hour before using tobacco. After waiting one hour, use tobacco as much as needed for the rest of the day.

(b) On day two, chew one piece of nicotine containing gum each hour for the first two hours after waking. Thereafter, use tobacco as much as needed the rest of the day.

(c) On each successive day, chew one piece of nicotine containing gum per hour for one hour longer than the previous day, and use tobacco as needed thereafter, using no more than 24 pieces of gum per day.

After four weeks, the individual will have stopped using tobacco but will continue using nicotine-containing gum to prevent cravings, according to the following schedule:

(a) In weeks 5–10, the individual uses one piece of nicotine containing gum every one to two hours;

(b) In weeks 11–13, the individual uses one piece of nicotine containing gum every two to four hours;

(c) In weeks 14–16, the individual uses one piece of nicotine containing gum every 4 to 8 hours; and (d) After week 16, the individual stops using nicotine-containing gum, except as needed to stay tobacco-free.

The efficacy of the method of this invention for smoking cessation by gradual reduction and in assisting smokers to gradually reduce the number of cigarettes smoked per day was demonstrated by a multi-center, randomized, double-blind, placebo-controlled, parallel group study. In this study, nicotine polacrilex gum (2 mg. or 4 mg. dosage) was administered to smokers meeting the entrance criteria. Smokers were approximately equally randomized to the 2 mg. and 4 mg. dosage groups (active and placebo). Study subjects self selected their gum dosage (2 mg or 4 mg treatment group) at Visit 1. No counseling or intervention was provided at any time by study personnel. Study subjects had study visits on Day 1, Weeks 2, 4, 8 and, if they were successful quitters, at Week 24. Study subjects were allowed 8 weeks to reduce their smoking and quit. A successful quitter was defined as a study subject that had continuous abstinence from smoking for 28 days and had two carbon monoxide measurements averaging less than or equal to 10 ppm measured after 2 PM, verified at an individual verification visit. The maximum duration of subject participation in the study was 6 months. Smoking and gum use were documented through use of questionnaires as Day 1 and Weeks 2, 4 and 8 and, if applicable, the individual verification visit. Smoking reduction at two weeks was measured by the number of cigarettes smoked per day, carbon monoxide level measurement and, at selected centers, serum thiocyanate levels.

The gum was chewed by the study subjects according to the directions described above. The Cochran-Mantel-Haenszel test, controlling for site, was used to compare the difference in smoking cessation rates between the two treatment groups for smokers who selected 2 mg. or 4 mg. nicotine gum, separately. The Cochran-Mantel-Haenszel test (general association version), controlling for nicotine gum dose level and site, was performed to compare the difference in smoking cessation rates between the two treatment groups for all smokers.

In all, a total of 3,297 subjects were randomized to the two treatment groups as follows:

| 2 mg. group | | 4 mg. group | |
|---|---|---|---|
| Total: | 1636 | Total: | 1661 |
| Placebo: | 817 | Placebo: | 830 |
| Active: | 819 | Active: | 831 |

Within the 2 mg. group, the success rates differed significantly between active (10.38%) and placebo subjects (5.39%). Subjects who received 2 mg. active nicotine gum were almost twice as likely to quit than subjects who received placebo gum. Within the 4 mg. group, the success rates differed significantly between active (10.60%) and placebo (2.53%) subjects. Subjects who received 4 mg. active nicotine gum were more than four times as likely to quit than subjects who received placebo gum.

The present invention is also directed to a method of reducing tobacco usage without necessarily eliminating it. In this embodiment, once an individual reaches the level of tobacco usage desired, the individual continues to use the desired amount of tobacco while continuing to use nicotine-containing gum at that particular level. For example, if the individual reduces smoking to smoking four cigarettes per day and chews twelve pieces of nicotine-containing gum per day, the individual can continue that regimen. Of course, this alternative embodiment does not preclude having reduction of tobacco usage as the ultimate goal and then immediately continuing the method described in the first embodiment to cessation of tobacco usage, or maintaining the reduction regimen for a period and then continuing the method, according to the first embodiment, to cessation of tobacco usage.

The methods described above are especially suited for modem smoking habits brought on by low tolerance for smoking as is found, for example, in a smoke-free workplace. The changing social views of smoking has forced smokers to consume tobacco less frequently and often in inhospitable environments. The steadily increasing use of an alternative nicotine source used in the above methods dulls the cravings that naturally arise during smokeless periods. Reduced cravings allow the user to stay within the plan more easily than if tobacco is eliminated entirely or if an alternative nicotine source is used only during time-spaced consumption periods.

The methods of this invention are also intended to be applicable to reduction and/or cessation of the use of tobacco products other than cigarettes, such as use of smokeless tobacco such as chewing tobacco and snuff.

Where the present invention is practiced using nicotine-containing gum as the alternative nicotine source, the individual should understand and be made aware that nicotine-containing gum is a pharmaceutical product and must be used in a certain way to gain the benefit of it and of the present invention. For example, the nicotine-containing gum should be chewed slowly until the individual notices a tingling sensation. Then, the individual should park the gum next to his or her cheek until the tingle is almost gone. After the tingle is gone, the individual should begin chewing again until the tingle returns, and then park the gum again. The individual should repeat this process until most of the tingle is gone, then discard the gum.

In the implementation of the methods according to the present invention, individuals were not provided with intensive instruction but were given only simple written instructions to follow setting forth the above steps. It has been found that the present methods overcome barriers in previous methods by showing the efficacy of nicotine replacement therapy for use in a gradual method of reduction or cessation of tobacco usage without intensive, face-to-face contact with a counselor or psychologist.

The foregoing description of present invention is presented for purposes of illustration and description. It is not intended to be exhaustive or to limit the present invention to the precise embodiments or steps disclosed. Obvious modifications or variations are possible in light of the above teachings. For example, various phases of the methods may be adjusted in length in order to reflect differences in the tobacco usage pattern of the individual. Further, alternative nicotine sources may include substances equivalent to or approximating nicotine including any and all known compounds and/or compositions, such as lobeline sulfate, that produce a similar physiological effect and may be substituted for the alternative nicotine source in accordance with the present invention. The above embodiments were chosen and described to provide the best illustration of the principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the breadth to which they are fairly, legally and equitably entitled.

What is claimed is:

1. A method of gradually reducing an individual's tobacco usage habit, comprising the steps of:
   (a) administering one unit of an alternative nicotine source after waking, waiting one hour, and then continuing the individual's normal tobacco usage pattern for a fast predetermined period of time;
   (b) administering one unit of an alternative nicotine source in each consecutive one hour time unit after waking, waiting one hour and then continuing the individual's normal tobacco usage pattern for a predetermined period of time to define a modified tobacco usage pattern;
   (c) repeating step (b) until a desired level of usage of said alternative nicotine source and a desired modified tobacco usage pattern is reached; and
   (d) maintaining said desired level of usage of said alternative nicotine source and said desired modified tobacco usage pattern,
      wherein the desired modified tobacco usage pattern and the desired level of said alternative nicotine source is not zero.

2. The method of claim 1, wherein said alternative nicotine source is absorbed through mucous membranes.

3. The method of claim 1, wherein said alternative nicotine source is selected from the group consisting of nicotine-containing gum, a nicotine-containing inhaler, a nicotine-containing lozenge, and nicotine nasal spray.

4. The method of claim 1, wherein said unit of alternative nicotine source is from about 2 mg to about 4 mg of nicotine.

5. The method of claim 1, wherein said alternative nicotine source is a unit of nicotine containing gum at a dosage of from about 2 milligrams to about 4 milligrams of nicotine.

6. A method of reducing an individual's nicotine usage habit, comprising the steps of:
   (a) administering one unit of an alternative nicotine source after waking, waiting one hour, and then continuing an individual's normal tobacco usage pattern for a first predetermined period of time;
   (b) administering one unit of an alternative nicotine source in each consecutive one hour time unit after waking, waiting one hour and then continuing the individual's normal tobacco usage pattern for a predetermined period of time to define a modified tobacco usage pattern;
   (c) repeating step (b) until the desired modified tobacco usage pattern is using no tobacco;
   (d) maintaining said desired level of usage of said alternative nicotine source,
      wherein the desired modified tobacco usage pattern and the desired level of said alternative nicotine source is not zero.

7. The method of claim 6 further comprising the step of gradually reducing the level of usage of said alternative nicotine source to a modified desired usage level, wherein said modified desired usage level is not zero.

8. The method of claim 6, wherein said alternative nicotine source is absorbed through mucous membranes.

9. The method of claim 6, wherein said alternative nicotine source is selected from the group consisting of nicotine-containing gum, a nicotine-containing inhaler, a nicotine-containing lozenge, and nicotine nasal spray.

10. The method of claim 6, wherein said unit of alternative nicotine source is from about 2 mg to about 4 mg of nicotine.

11. The method of claim 6, wherein said alternative nicotine source is a unit of nicotine containing gum at a dosage of from about 2 milligrams Lo about 4 milligrams of nicotine.

* * * * *